United States Patent
Honda

(10) Patent No.: US 8,579,836 B2
(45) Date of Patent: *Nov. 12, 2013

(54) TREATMENT APPARATUS AND OPERATION SYSTEM

(75) Inventor: Yoshitaka Honda, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/416,651

(22) Filed: Mar. 9, 2012

(65) Prior Publication Data

US 2012/0172767 A1 Jul. 5, 2012

Related U.S. Application Data

(63) Continuation of application No. PCT/JP2009/066319, filed on Sep. 11, 2009.

(51) Int. Cl.
*A61H 1/00* (2006.01)

(52) U.S. Cl.
USPC .................................................. 601/3

(58) Field of Classification Search
USPC .................................................. 601/3
See application file for complete search history.

(56) References Cited

U.S. PATENT DOCUMENTS

| | | | | |
|---|---|---|---|---|
| 5,195,959 A * | 3/1993 | Smith | ............................ | 604/34 |
| 2002/0194907 A1* | 12/2002 | Bostrom et al. | ........... | 73/152.58 |
| 2003/0018256 A1* | 1/2003 | Sasaki et al. | ................. | 600/439 |
| 2005/0234446 A1* | 10/2005 | Van Wyk et al. | ............... | 606/41 |
| 2006/0012770 A1* | 1/2006 | Dierichs | ........................ | 355/71 |
| 2007/0161902 A1* | 7/2007 | Dan | .............................. | 600/458 |
| 2008/0194999 A1* | 8/2008 | Yamaha et al. | ................... | 601/2 |
| 2009/0036914 A1 | 2/2009 | Houser | | |
| 2009/0138027 A1 | 5/2009 | Lucas et al. | | |

FOREIGN PATENT DOCUMENTS

| | | |
|---|---|---|
| JP | 9-501080 | 2/1997 |
| JP | 2001253836 A | 9/2001 |
| JP | 2008-188160 | 8/2008 |
| WO | WO 98/51224 A2 | 11/1998 |
| WO | WO 00/00095 A1 | 1/2000 |
| WO | WO 2004/060448 A2 | 7/2004 |

OTHER PUBLICATIONS

English Abstract of International Publication No. WO 95/03740, dated Feb. 9, 1995.
International Search Report dated Apr. 8, 2010 issued in PCT/JP2009/066319.

* cited by examiner

*Primary Examiner* — Tse Chen
*Assistant Examiner* — Hien Nguyen
(74) *Attorney, Agent, or Firm* — Scully, Scott, Murphy & Presser, P.C.

(57) ABSTRACT

A treatment apparatus of the present invention includes a treatment section that performs treatment of a treatment target region of a treatment subject, a detection section that detects cavitations that are generated in accordance with a treatment of the treatment section, and a control section that controls a generation state of cavitations at the treatment target region by controlling a physico-chemical parameter of the treatment section based on a detection result at the detection section.

5 Claims, 8 Drawing Sheets

TREATMENT APPARATUS AND OPERATION SYSTEM

CROSS REFERENCE TO RELATED APPLICATION

This application is a continuation application of PCT/JP2009/066319 filed on Sep. 11, 2009, the entire contents of which are incorporated herein by this reference.

BACKGROUND OF THE INVENTION

1. Field of the Invention

The present invention relates to a treatment apparatus and an operation system that perform treatment utilizing cavitations.

2. Description of the Related Art

Apparatuses (hereafter, referred to as "ultrasound treatment apparatuses") that perform treatment with respect to living tissue by utilizing ultrasound vibrations or various phenomena that arise accompanying ultrasound vibrations are already widely known. As an example of such kind of apparatus, an ultrasound operation device disclosed in Japanese Patent Application Laid-Open Publication No. 2008-188160 may be mentioned.

It is considered that the treatment capability of an ultrasound treatment apparatus depends greatly on the state of cavitation generation at a treatment target region. Therefore, in order to perform treatment efficiently using an ultrasound treatment apparatus, control that causes cavitations being generated at a treatment target region to be generated in an appropriate state in accordance with the contents of a treatment is essential.

SUMMARY OF THE INVENTION

A treatment apparatus of the present invention has a treatment section that performs treatment of a treatment target region of a treatment subject; a detection section that detects cavitations that are generated in accordance with a treatment of the treatment section; and a control section that controls a generation state of cavitations at the treatment target region by controlling a physico-chemical parameter of the treatment section based on a detection result at the detection section.

An operation system of the present invention has an ultrasound transducer that is capable of generating ultrasound vibrations; a drive section that drives the ultrasound transducer by means of a drive signal; a probe that has a proximal end portion that is mechanically connected with the ultrasound transducer, and a distal end portion that can be brought adjacent to or in contact with a treatment target region of a treatment subject, the probe being capable of transmitting ultrasound vibrations generated at the ultrasound transducer from the proximal end portion to the distal end portion; a physico-chemical parameter adjustment section that changes a physico-chemical parameter of the distal end portion; a detection section that detects a physical quantity that changes due to cavitations that are generated at the treatment target region by ultrasound vibrations of the distal end portion, based on the drive signal that is supplied to the ultrasound transducer; and a control section that controls a generation state of cavitations at the treatment target region by controlling the physico-chemical parameter adjustment section based on a detection result of the detection section.

DETAILED DESCRIPTION OF THE PREFERRED EMBODIMENTS

An embodiment of the present invention is described hereunder with reference to the drawings.

Figure 1:
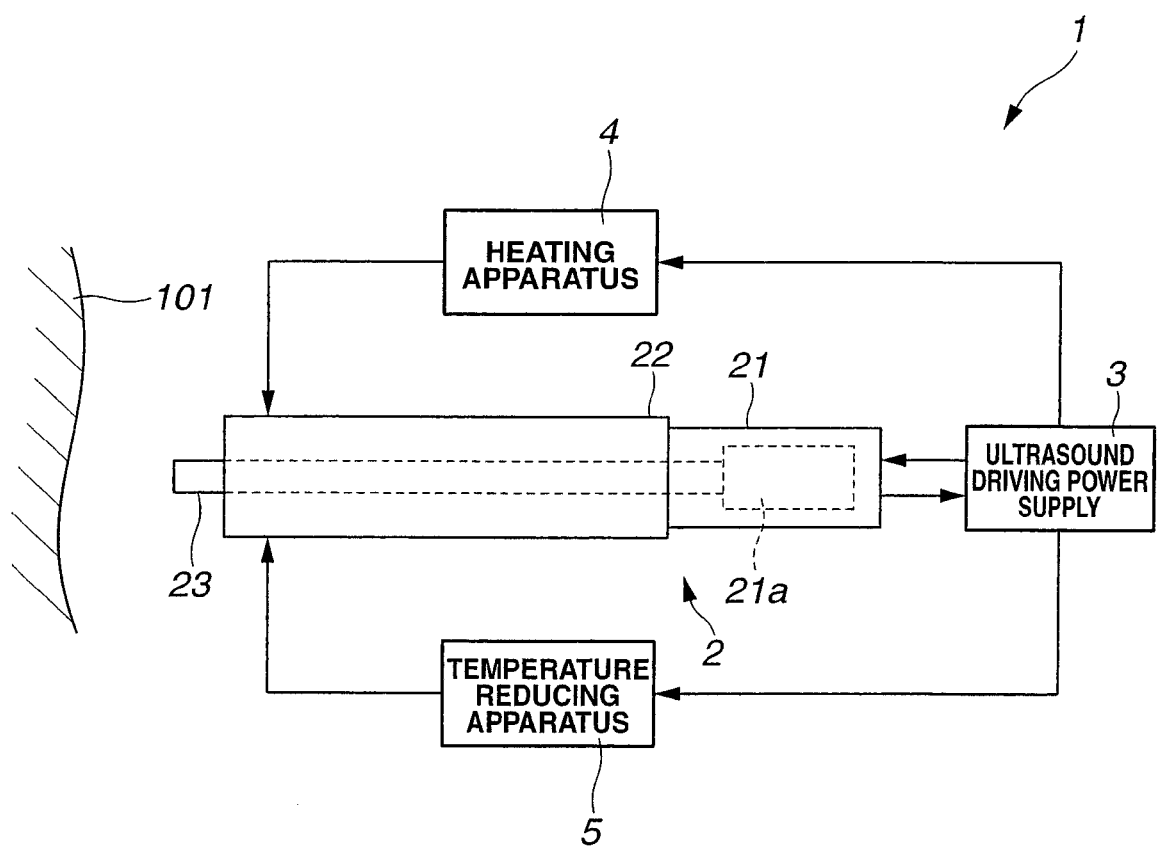
FIG. 1 is a view that shows an example of the configuration of an operation system according to an embodiment of the present invention.

As shown in FIG. 1, an operation system 1 has an ultrasound treatment handpiece 2 that performs treatment by causing ultrasound vibrations to act on living tissue of a treatment target region 101, an ultrasound driving power supply 3 that supplies an ultrasound drive signal for driving the ultrasound treatment handpiece 2, a heating apparatus 4, and a temperature reducing apparatus 5.

The ultrasound treatment handpiece 2 is equipped with a function as a cavitation generation section, and includes a grasping section 21 that is grasped by a surgeon or the like, a sheath 22 that is provided in a linked manner with respect to a distal end side of the grasping section 21, and a probe 23 having a distal end portion that protrudes from the distal end side of the sheath 22. The distal end portion of the probe 23 is equipped with a function as a treatment section.

The ultrasound treatment handpiece 2 is equipped with a heating function (heating means) that is capable of raising a temperature (promoting generation of thermal energy) of the distal end portion of the probe 23 and/or a temperature in a vicinity of the distal end portion in response to operation of the heating apparatus 4. The ultrasound treatment handpiece 2 is also equipped with a temperature reducing function (temperature reducing means) that is capable of lowering the temperature (suppressing generation of thermal energy) of the distal end portion of the probe 23 and/or the temperature in the vicinity of the distal end portion in response to operation of the temperature reducing apparatus 5. Further, the ultrasound treatment handpiece 2 is equipped with a temperature information output function (temperature information output means) that is capable of outputting temperature information with respect to the distal end portion of the probe 23 and/or the vicinity of the distal end portion as a temperature signal. In this connection, specific configurations for implementing these three functions (means) and the actions thereof are described in detail later.

An ultrasound transducer 21a is provided inside the grasping section 21. The ultrasound transducer 21a is equipped with a predetermined resonance frequency and is mechanically connected to the proximal end portion of the probe 23, and generates ultrasound vibrations in accordance with an ultrasound drive signal that is supplied from the ultrasound driving power supply 3. The probe 23 transmits ultrasound vibrations that are generated by the ultrasound transducer 21a from the proximal end portion of the probe 23 to the distal end portion thereof.

More specifically, ultrasound vibrations generated at the ultrasound transducer 21a are transmitted to the distal end portion of the probe 23 after passing a midway portion of the probe 23.

The sheath 22 contains therein (one part of) the proximal end portion and the midway portion of the probe 23.

Figure 2:
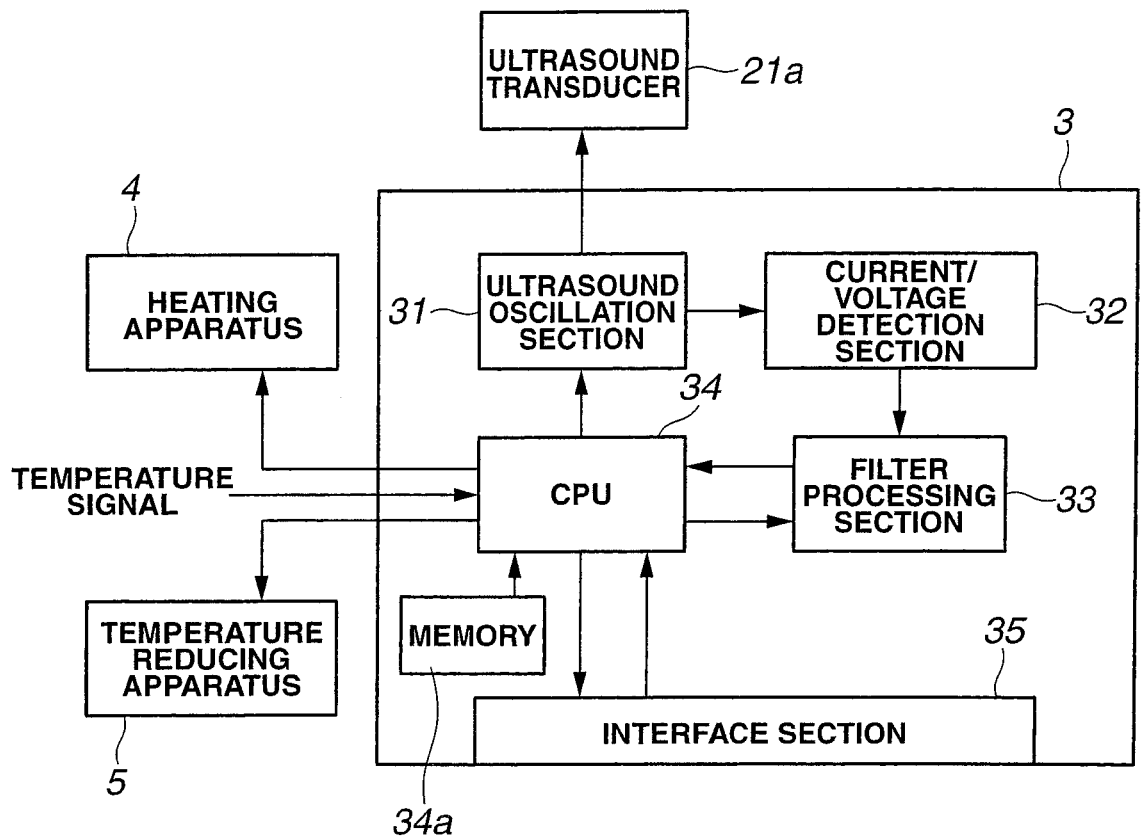
FIG. 2 is a block diagram that shows an example of the specific configuration of an ultrasound driving power supply shown in FIG. 1.

As shown in FIG. 2, the ultrasound driving power supply 3 has an ultrasound oscillation section 31 that generates and outputs an ultrasound drive signal for driving the ultrasound transducer 21a that is equipped with a predetermined resonance frequency, a current/voltage detection section 32 that detects, at a predetermined frequency band, a magnitude of a current or a voltage of an ultrasound drive signal that is outputted from the ultrasound oscillation section 31, a filter processing section 33 that performs filter processing on a detection result obtained by the current/voltage detection section 32, a CPU 34 that is equipped with a function as a control section, a memory 34a, and an interface section 35.

Figure 3:
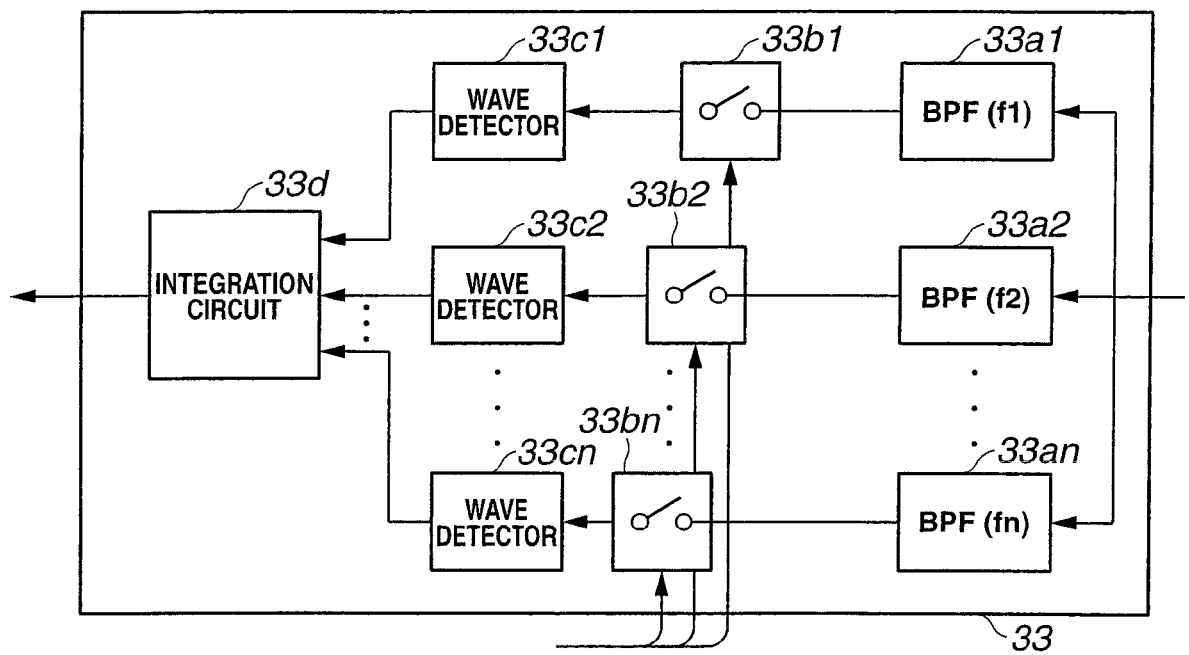
FIG. 3 is a block diagram that shows an example of the specific configuration of a filter processing section shown in FIG. 2.

As shown in FIG. 3, the filter processing section 33 includes n bandpass filters (in FIG. 3, abbreviated as "BPF") $33a1, 33a2, \ldots, 33an$ into which a detection result from the current/voltage detection section 32 is inputted, respectively; n switches $33b1, 33b2, \ldots, 33bn$ that are connected one-to-one with a post stage of the n bandpass filters; n wave detectors $33c1, 33c2, \ldots, 33cn$ that are connected one-to-one with a post stage of each of the n switches; and an integrator $33d$ into which output signals from the n wave detectors are inputted.

The bandpass filters $33a1, 33a2, \ldots, 33an$ are, for example, configured as filters in which parts (ends) of the passing frequency bands mutually overlap and in which center frequencies of the passing frequency bands are respectively different. In this connection, in FIG. 3, the center frequencies of the passing frequency bands of the bandpass filters $33a1, 33a2, \ldots, 33an$ are denoted as $f1, f2, \ldots, fn$ (provided, it is assumed that $f1 < f2 < \ldots < fn$).

Figure 4:
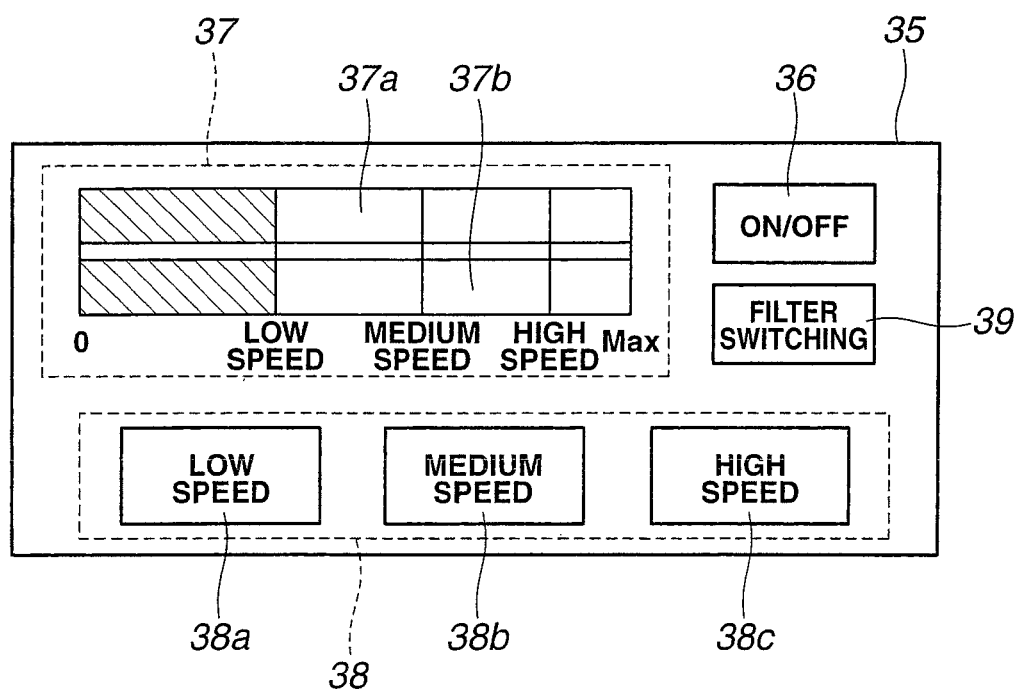
FIG. 4 is a view that shows an example of the specific configuration of an interface section shown in FIG. 2.

Hereafter, FIG. 4 is also utilized to facilitate the description of this embodiment. The switches $33b1, 33b2, \ldots, 33bn$ are switched on or off by the CPU 34 performing control based on a switching instruction of a filter switching switch 39 provided in the interface section 35. In this connection, a configuration may also be adopted such that the switches $33b1, 33b2, \ldots, 33bn$ are switched on or off directly in response to a switching instruction from the filter switching switch 39.

Frequency components that pass through the switches $33b1, 33b2, \ldots, 33bn$ that are in an "on" state are detected by the wave detectors $33c1, 33c2, \ldots, 33cn$, respectively, and thereafter subjected to integration processing by the integrator $33d$.

The integrator $33d$ outputs a processing result of the aforementioned integration processing as a cavitation detection signal to the CPU 34. In this connection, the filter processing section 33 of the present embodiment may be configured using an accumulator instead of the integrator $33d$. Further, in the present embodiment, the aforementioned integration processing may be performed by the CPU 34 instead of the integrator $33d$.

The CPU 34 appropriately controls the operations of the heating apparatus 4 and the temperature reducing apparatus 5 as required based on a temperature signal that is outputted in response to operation of the temperature information output function (temperature information output means) of the ultrasound treatment handpiece 2, a cavitation detection signal that is outputted from the filter processing section 33, and a switched state of each switch of a treatment speed switching section 38 provided in the interface section 35.

In this case, setting data that shows a correlation between switches that are switched on at the treatment speed switching section 38 and an appropriate cavitation generation state corresponding to the switches is previously stored in the memory 34a.

More specifically, when a switch (a switch 38a described later) that sets a treatment speed to a low speed is switched on at the treatment speed switching section 38, setting data that sets the generation state of cavitations to a first level is stored in the memory 34a. Further, when a switch (a switch 38b described later) that sets a treatment speed to a medium speed is switched on at the treatment speed switching section 38, setting data that sets the generation state of cavitations to a second level is stored in the memory 34a. Furthermore, when a switch (a switch 38c described later) that sets a treatment speed to a high speed is switched on at the treatment speed switching section 38, setting data that sets the generation state of cavitations to a third level is stored in the memory 34a. In this connection, it is assumed that a relationship is established between each of these kinds of setting data whereby the first level<second level<third level so that the amount of generated cavitations increases accompanying an increase in the treatment speed.

With respect to setting data that sets the generation state of cavitations to the first level, as a setting that makes a temperature of the distal end portion of the probe 23 and/or in a vicinity of the distal end portion a first temperature, for example, a setting is made that makes the heating apparatus 4 operate normally and makes the temperature reducing apparatus 5 operate at a higher output than at normal operation. Further, with respect to setting data that sets the generation state of cavitations to the second level, as a setting that makes a temperature of the distal end portion of the probe 23 and/or in the vicinity of the distal end portion a second temperature, for example, a setting is made that causes both the heating apparatus 4 and the temperature reducing apparatus 5 to operate normally. Furthermore, with respect to setting data that sets the generation state of cavitations to the third level, as a setting that makes a temperature of the distal end portion of the probe 23 and/or in the vicinity of the distal end portion a third temperature, for example, a setting is made that makes the heating apparatus 4 operate at a higher output than at normal operation and makes the temperature reducing apparatus 5 operate normally. In this connection, it is assumed that a relationship is established with respect to these settings such that the first temperature<second temperature<third temperature.

More specifically, the CPU 34 previously reads in (for example, immediately after the power of the ultrasound driving power supply 3 is turned on) the respective setting data that is stored in the memory 34a, and appropriately performs operational control with respect to the heating apparatus 4 and the temperature reducing apparatus 5 based on a temperature signal that is outputted in accordance with operation of the temperature information output function (temperature information output means) of the ultrasound treatment handpiece 2, a cavitation detection signal that is outputted from the filter processing section 33, and a switched state of each switch of the treatment speed switching section 38 provided in the interface section 35 while referring to the respective setting data that is read from the memory 34a.

Based on the switched state of each switch of the treatment speed switching section 38 provided in the interface section 35, the CPU 34 outputs a first display control signal for changing a display state of an indicator 37a provided in the interface section 35.

Based on a cavitation detection signal that is outputted from the filter processing section 33, as necessary the CPU 34 outputs a second display control signal for changing a display state of an indicator 37b provided in the interface section 35.

Based on a switched state of an ultrasound vibrations switching switch 36 provided in the interface section 35, the CPU 34 performs control for switching on or off the operating state of the ultrasound oscillation section 31 that is equipped with a function as a drive section.

Based on a switching instruction of the filter switching switch 39 provided in the interface section 35, the CPU 34 performs control for switching the switches 33b1, 33b2, . . . , 33bn of the filter processing section 33 on or off, respectively.

As shown in FIG. 4, the interface section 35 has the ultrasound vibrations switching switch 36 that is capable of switching ultrasound vibrations on or off in accordance with an operation of a surgeon or the like; an information presentation section 37 that visually shows information relating to a setting value and a measurement value of a cavitation generation state; the treatment speed switching section 38 that is capable of switching a treatment speed with respect to the treatment target region 101 in accordance with an operation of the surgeon or the like; and the filter switching switch 39 that is capable of switching a filter to be used in filter processing of the filter processing section 33 in accordance with an operation of the surgeon or the like. Each section of the interface section 35 described above is provided, for example, on a front panel of the ultrasound driving power supply 3.

The information presentation section 37 includes the indicator 37a that visually shows a setting value of a cavitation generation state and the indicator 37b that visually shows a measurement value of a cavitation generation state.

The treatment speed switching section 38 includes the switch 38a that is capable of issuing an instruction to set a treatment speed with respect to the treatment target region 101 to a low speed, the switch 38b that is capable of issuing an instruction to set a treatment speed with respect to the treatment target region 101 to a medium speed, and the switch 38c that is capable of issuing an instruction to set a treatment speed with respect to the treatment target region 101 to a high speed.

The indicator 37a changes its own display state in accordance with an output state of the first display control signal from the CPU 34. More specifically, when the switch 38a is turned on, for example (as shown in FIG. 4), the indicator 37a enters a display state in which a portion corresponding to "0" to "low speed" in a display area from a "0" graduation on a left end to a "Max" graduation on a right end is colored uniformly or substantially uniformly. Further, when the switch 38b is turned on, for example, the indicator 37a enters a display state in which a portion corresponding to "0" to "medium speed" in the display area from the "0" graduation on the left end to the "Max" graduation on the right end is colored uniformly or substantially uniformly. Furthermore, when the switch 38c is turned on, for example, the indicator 37a enters a display state in which a portion corresponding to "0" to "high speed" in the display area from the "0" graduation on the left end to the "Max" graduation on the right end is colored uniformly or substantially uniformly.

The indicator 37b changes its own display state in real time in accordance with an output state of the second display control signal from the CPU 34. More specifically, the indicator 37b enters a display state in which a portion from "0" to a part that corresponds to a level of the aforementioned cavitation detection signal in the display area from the "0" graduation on the left end to the "Max" graduation on the right end is colored uniformly or substantially uniformly. For example, a display state of the indicator 37b when the second display control signal is outputted in a case when the level of the aforementioned cavitation detection signal corresponds to "low speed" is as shown in FIG. 4.

In this connection, the indicators 37a and 37b may be indicators that are displayed as images on an LCD panel, or may be configured using a luminescent member such as an LED. (When the indicators 37a and 37b are configured using a luminescent member such as an LED, information relating to a setting value and a measurement value of a cavitation generation state can be displayed by means of the presence or absence of lighting instead of the presence or absence of coloring.)

The heating apparatus 4 is configured to be capable of activating a heating function (heating means) of the ultrasound treatment handpiece 2 based on control of the ultrasound driving power supply 3. More specifically, the heating apparatus 4 includes, for example, a DC variable power supply that is capable of changing an output so as to raise and/or stabilize a temperature of the distal end portion of the probe 23 and/or a temperature in the vicinity of the distal end portion based on control of the ultrasound driving power supply 3.

The temperature reducing apparatus 5 is configured to be capable of activating the temperature reducing function (temperature reducing means) of the ultrasound treatment handpiece 2 based on control of the ultrasound driving power supply 3. More specifically, the temperature reducing apparatus 5 includes, for example, a pump and a coolant tank that are capable of changing a supply amount of a coolant that is supplied to the distal end portion of the probe 23 and/or the vicinity of the distal end portion based on control of the ultrasound driving power supply 3. In this connection, the coolant that is supplied from the temperature reducing apparatus 5 may be a cooling liquid or a cooling gas.

In this connection, it is assumed that a temperature adjustment section of the present embodiment is configured to include the heating apparatus 4 and the temperature reducing apparatus 5. Further, it is assumed that a thermal energy adjustment section of the present embodiment is configured to include the heating apparatus 4 and the temperature reducing apparatus 5.

Operations and the like of the operation system 1 of the present embodiment will now be described.

First, while grasping the grasping section 21, a surgeon performs an operation to bring the distal end portion of the probe 23 close to the treatment target region 101. Further, by switching the ultrasound vibrations switching switch 36 from "off" to "on" before or after the aforementioned operation, the surgeon starts the generation of ultrasound vibrations at the distal end portion of the probe 23. In this connection, the following description is based on an assumption that treatment is being performed in a state in which an output level of ultrasound vibrations at the distal end portion of the probe 23 (output level of an ultrasound drive signal that is outputted from the ultrasound oscillation section 31) is maintained at a fixed level.

Next, for example, in order to set a treatment speed with respect to the treatment target region 101, the surgeon switches any single switch among the switches provided in the treatment speed switching section 38 from "off" to "on".

Upon the operations described above being performed, generation of cavitations begins at the treatment target region 101 and treatment with respect to living tissue of the treatment target region 101 starts.

Specific configuration examples for implementing the aforementioned three functions (means) including the heating function (heating means), the temperature reducing function (temperature reducing means), and the temperature information output function (temperature information output means) at the ultrasound treatment handpiece will now be described. In this connection, the description of each of the configuration examples described hereunder is based on an assumption that, particularly with regard to portions that are not described in detail, components of the configuration examples are the same as those described above as components of the ultrasound treatment handpiece 2.

First Configuration Example

Figure 5:
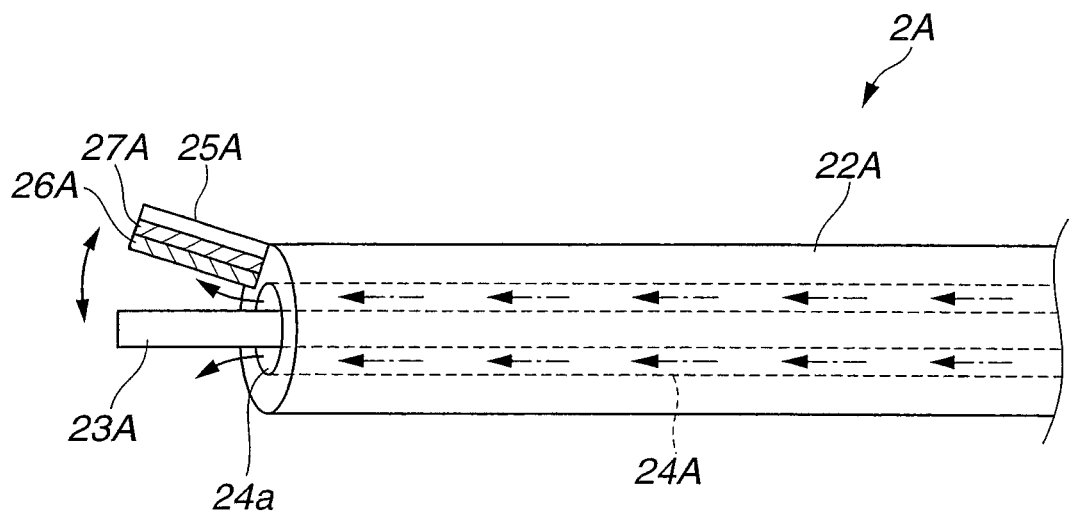
FIG. 5 is a view that shows a first configuration example of an ultrasound treatment handpiece.

FIG. 5 is a view that illustrates a first configuration example of an ultrasound treatment handpiece.

In an ultrasound treatment handpiece 2A shown in FIG. 5, a sheath 22A is provided in a linked manner with respect to a distal end side of an unshown grasping section that is grasped by a surgeon or the like, and a conduit 24A is formed inside the sheath 22A. The ultrasound treatment handpiece 2A has a configuration that enables a probe 23A to be inserted through the inside of the conduit 24A. A distal end portion of the probe 23A that is equipped with a function as a treatment section is disposed so as to protrude from an opening portion 24a that is provided in a distal end face of the sheath 22A when treatment with respect to the treatment target region 101 is started.

One end of the conduit 24A communicates with the opening portion 24a. Another end of the conduit 24A communicates with the temperature reducing apparatus 5. According to this configuration, since coolant that is supplied to the conduit 24A of the ultrasound treatment handpiece 2A from the temperature reducing apparatus 5 is released via the opening portion 24a, a temperature of the distal end portion of the probe 23A that is protruded from the opening portion 24a and a temperature in a vicinity of the distal end portion can be lowered (generation of thermal energy can be suppressed).

At a distal end portion of the sheath 22A, a jaw 25A is provided that opens/closes in accordance with an operation of an unshown handle or the like that is provided in the unshown grasping section.

More specifically, in the ultrasound treatment handpiece 2A shown in FIG. 5, treatment of the living tissue is performed by sandwiching and holding living tissue of the treatment target region 101 between the distal end portion of the probe 23A and the jaw 25A while ultrasound vibrations are being generated.

In the jaw 25A, a temperature sensor 26 is provided at a portion that directly contacts living tissue of the treatment target region 101. The temperature sensor 26 is connected to the CPU 34 of the ultrasound driving power supply 3 through an unshown signal wire that is inserted through the inside of the sheath 22A. According to this configuration, the temperature sensor 26 can acquire temperature information for the vicinity of the distal end portion of the probe 23A that is protruded from the opening portion 24a and output the acquired temperature information as a temperature signal to the CPU 34 of the ultrasound driving power supply 3.

In the jaw 25A, a heater element 27A is provided at a portion adjacent to the temperature sensor 26. The heater element 27A is connected to the heating apparatus 4 through an unshown heating wire or signal wire that is inserted through the inside of the sheath 22A. According to this configuration, since the heater element 27A generates heat in accordance with a magnitude of a voltage and/or a current that has been outputted from the heating apparatus 4, a temperature of the distal end portion of the probe 23A that is protruded from the opening portion 24a and a temperature of a vicinity of the distal end portion can be raised (generation of thermal energy can be promoted).

Figure 6:
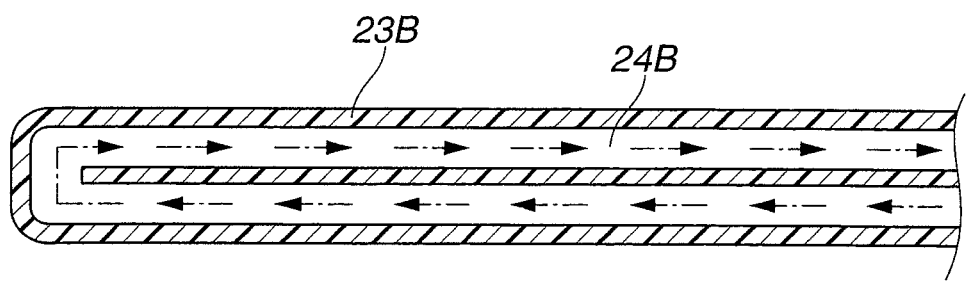
FIG. 6 is a view that shows a specific configuration example of another probe that is different to the probe shown in FIG. 5.

In this connection, the temperature reducing function (temperature reducing means) of the ultrasound treatment handpiece 2A shown in FIG. 5 is not limited to a function (means) that is implemented by the aforementioned configuration, and may also be implemented using a probe 23B as shown in FIG. 6.

The probe 23B, for example, includes therein a conduit 24B as shown in FIG. 6, and has the same configuration as the probe 23A with respect to portions other than the conduit 24B. The conduit 24B contained inside the probe 23B has a configuration such that, after coolant supplied from the temperature reducing apparatus 5 has been circulated as far as a distal end portion, the coolant that has reached the distal end portion of the probe 23B can be recirculated back to the temperature reducing apparatus 5. According to this configuration, it is possible to lower from inside the probe 23B a temperature of the distal end portion of the probe 23B that is equipped with a function as a treatment section by means of coolant that is supplied to the conduit 24B from the temperature reducing apparatus 5 (generation of thermal energy can be suppressed from inside).

Second Configuration Example

Figure 7:
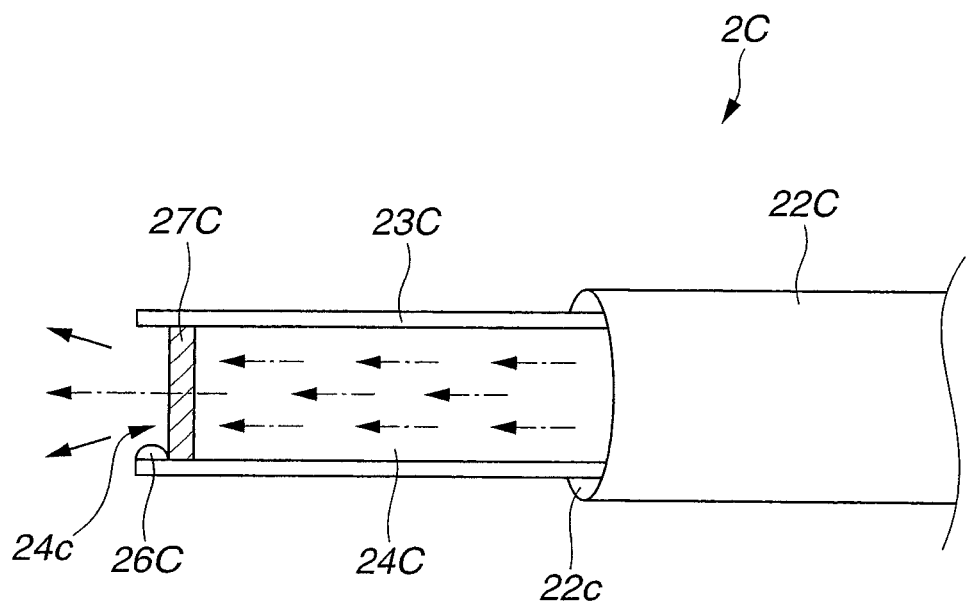
FIG. 7 is a view that shows a second configuration example of the ultrasound treatment handpiece.

FIG. 7 is a view that illustrates a second configuration example of the ultrasound treatment handpiece.

In an ultrasound treatment handpiece 2C shown in FIG. 7, a hollow-shaped sheath 22C is provided in a linked manner with respect to a distal end side of an unshown grasping section that is grasped by a surgeon or the like. The ultrasound treatment handpiece 2C has a configuration that enables a probe 23C to be inserted through the hollow part of the sheath 22C. A distal end portion of the probe 23C that is equipped with a function as a treatment section is disposed so as to protrude from an opening portion 22c of the distal end side of the hollow-shaped sheath 22C when treatment for the treatment target region 101 is started. Further, a conduit 24C that has an opening portion 24c at a distal end side is provided inside the probe 23C.

On the inner circumferential face of the opening portion 24c, a temperature sensor 26 is provided at a position that contacts or comes close to living tissue of the treatment target region 101. The temperature sensor 26 is connected to the CPU 34 of the ultrasound driving power supply 3 through an unshown signal wire that is inserted through the inside of the sheath 22C. According to this configuration, the temperature sensor 26 can acquire temperature information for the vicinity of the distal end portion of the probe 23C that is protruded from the opening portion 22c and output the acquired temperature information as a temperature signal to the CPU 34 of the ultrasound driving power supply 3.

One end of the conduit 24C communicates with the opening portion 24c. Another end of the conduit 24C communicates with the temperature reducing apparatus 5.

A heater pattern 27C that has a mesh pattern along an open face of the opening portion 24c is disposed at a position adjacent to the temperature sensor 26 of the opening portion 24c. The heater pattern 27C is connected to the heating apparatus 4 through an unshown heating wire that is inserted through the inside of the probe 23C.

According to the configuration described above, after coolant that is supplied to the conduit 24C of the ultrasound treatment handpiece 2C from the temperature reducing apparatus 5 passes through the heater pattern 27C, the coolant is released from the opening portion 24c. Further, according to the configuration described above, the heater pattern 27C generates heat in accordance with a magnitude of a voltage and/or a current that has been outputted from the heating apparatus 4.

Thus, according to the configuration described above, when coolant that has passed through the heater pattern 27C (for example, coolant that has been utilized to the extent of completely losing a function as coolant) is released from the opening portion 24c in a state in which the coolant has been amply heated, a temperature of the distal end portion of the probe 23C that is protruded from the opening portion 22c and a temperature of a vicinity of the distal end portion can be raised (generation of thermal energy can be promoted). In contrast, according to the configuration described above, when coolant that has passed through the heater pattern 27C (for example, coolant that has only been utilized to a degree to which the coolant maintains a function as coolant) is released from the opening portion 24c in a state in which the coolant has not been amply heated, a temperature of the distal end portion of the probe 23C that is protruded from the opening portion 22c and a temperature of a vicinity of the distal end portion can be lowered (generation of thermal energy can be suppressed).

Third Configuration Example

Figure 8:
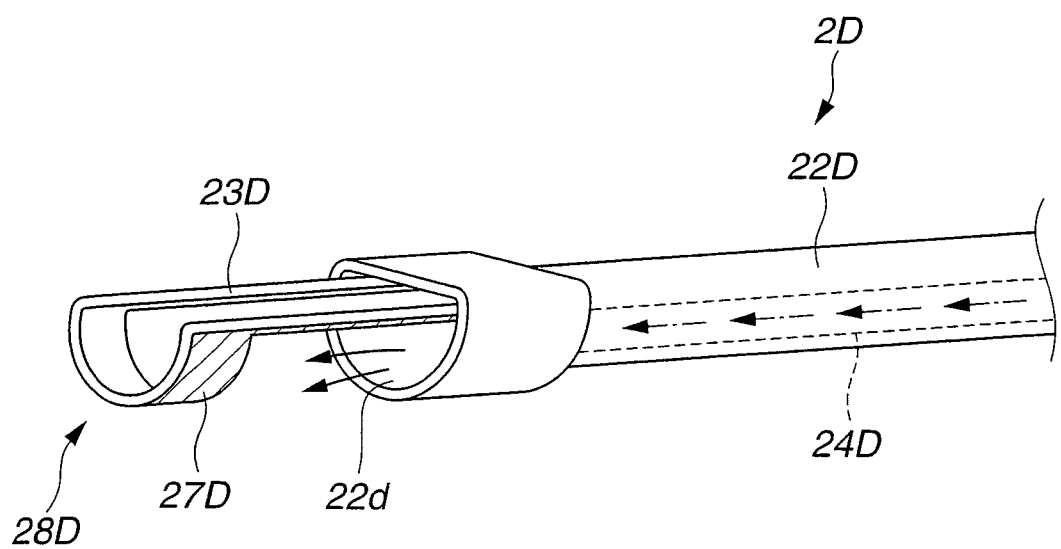
FIG. 8 is a view that shows a third configuration example of the ultrasound treatment handpiece.

FIG. 8 is a view that illustrates a third configuration example of the ultrasound treatment handpiece.

In an ultrasound treatment handpiece 2D shown in FIG. 8, a sheath 22D is provided in a linked manner with respect to a distal end side of an unshown grasping section that is grasped by a surgeon or the like, and a conduit 24D is formed inside the sheath 22D. A distal end portion of a probe 23D is disposed so as to protrude from an opening portion 22d of a distal end side of the sheath 22D when treatment with respect to the treatment target region 101 is started. Further, a treatment section 28D for performing treatment with respect to the living tissue of the treatment target region 101 is provided at the distal end portion of the probe 23D that is equipped with a function as a treatment section.

One end of the conduit 24D communicates with the opening portion 22d. Another end of the conduit 24D communicates with the temperature reducing apparatus 5. According to this configuration, since coolant that is supplied to the conduit 24D of the ultrasound treatment handpiece 2D from the temperature reducing apparatus 5 is released via the opening portion 22d, a temperature of the treatment section 28D that is protruded from the opening portion 22d and a temperature in a vicinity of the treatment section 28D can be lowered (generation of thermal energy can be suppressed).

As shown, for example, in FIG. 8, the treatment section 28D is configured as a plate member curved in a substantially semicircular shape that is suspended between the distal end portion of two arms that are disposed substantially in parallel. On the outside face of the curve of the plate member is provided a heater 27D that is formed by a member that has a positive temperature coefficient (PTC). The heater 27D is connected to the heating apparatus 4 through an unshown signal wire that is inserted through the inside of the probe 23D. According to this configuration, since the heater 27D generates heat in accordance with a magnitude of a voltage and/or a current that has been outputted from the heating apparatus 4, a temperature of the treatment section 28D that is protruded from the opening portion 22d and a temperature in a vicinity of the treatment section 28D can be raised (generation of thermal energy can be promoted).

Further, according to the configuration described above, since a resistance value of the heater 27D and a temperature of the treatment section 28D fluctuate while having a positive correlation, a detection result regarding the resistance value of the heater 27D can be regarded as temperature information of the treatment section 28D. More specifically, according to the ultrasound treatment handpiece 2D of the third configuration example, a temperature information output function (temperature information output means) can be implemented by a configuration that outputs a temperature signal that includes the aforementioned temperature information to the CPU 34 of the ultrasound driving power supply 3.

A description will now be given regarding control and the like that is performed at the operation system 1 of the present embodiment. In this connection, the following description is based on a premise that the same control and the like is performed in the case of adopting any configuration among the first to third configuration examples described above. Therefore, in order to encompass at least the aforementioned first to third configuration examples, the following description is based on an assumption that the ultrasound treatment handpiece 2 shown in FIG. 1 is equipped with a heating function (heating means), a temperature reducing function (temperature reducing means), and a temperature information output function (temperature information output means).

Figure 9:
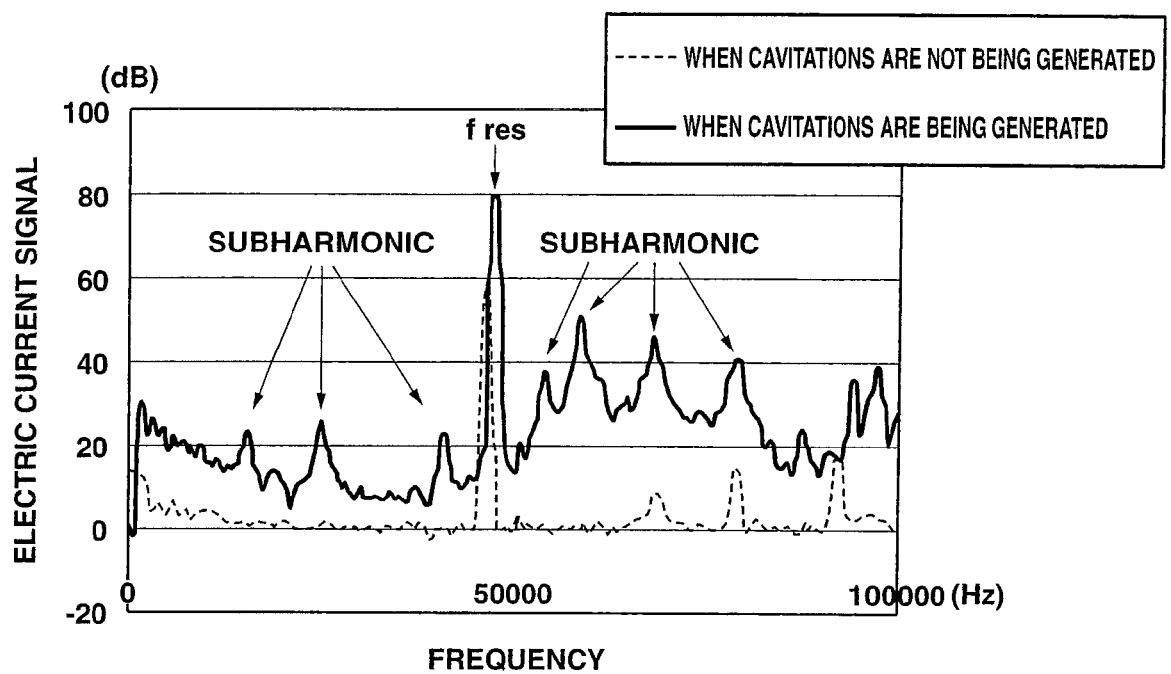
FIG. 9 is a view that shows an example of a detection result at a current/voltage detection section shown in FIG. 2.

When generation of cavitations begins at the treatment target region 101 and treatment with respect to living tissue of the treatment target region 101 is started, the current/voltage detection section 32 detects a magnitude of a current of an ultrasound drive signal that is outputted from the ultrasound oscillation section 31, for example, as a detection result illustrated in FIG. 9.

FIG. 9 is a view that shows detection results for magnitudes of a current of an ultrasound drive signal at the current/voltage detection section 32 as a frequency spectrum distribution. In this connection, in FIG. 9, a resonance frequency fres is set as 47 kHz. Further, in FIG. 9, (for comparison) a frequency spectrum distribution when cavitations are not being generated is shown by a broken line, and a frequency spectrum distribution when cavitations are being generated is shown by a solid line.

According to the detection results for magnitudes of a current exemplified in FIG. 9, the largest peak is detected at the resonance frequency fres, regardless of whether or not cavitations are generated.

Further, according to the detection results for the magnitudes of a current exemplified in FIG. 9, when cavitations are being generated a number of noticeable peaks are detected at frequency components other than the resonance frequency fres, and when cavitations are not being generated, noticeable peaks are not detected at frequency components other than the resonance frequency fres.

Specifically, as shown in FIG. 9, when cavitations are being generated, a level of subharmonics corresponding to frequencies of divisors such as ½ or ¼ of the resonance frequency fres or of differences of these divisors becomes particularly higher in comparison to when cavitations are not being generated, and a level of frequency components other than the subharmonics also becomes higher in a substantially uniform manner. Therefore, a generation state of cavitations at the treatment target region 101 can be detected by detecting a signal level of a frequency band excluding a vicinity of the resonance frequency fres in the detection result for magnitudes of a current of an ultrasound drive signal at the current/voltage detection section 32.

In this connection, in the operation system 1 of the present embodiment, a detection result for magnitudes of a current of an ultrasound drive signal and a detection result for magnitudes of a voltage of the ultrasound drive signal exhibit substantially the same trends. Therefore, even when a detection result for magnitudes of a voltage of the ultrasound drive signal are used instead of a detection result for magnitudes of a current of the ultrasound drive signal, the processing and operations described below can be performed in substantially the same manner.

Figure 10:
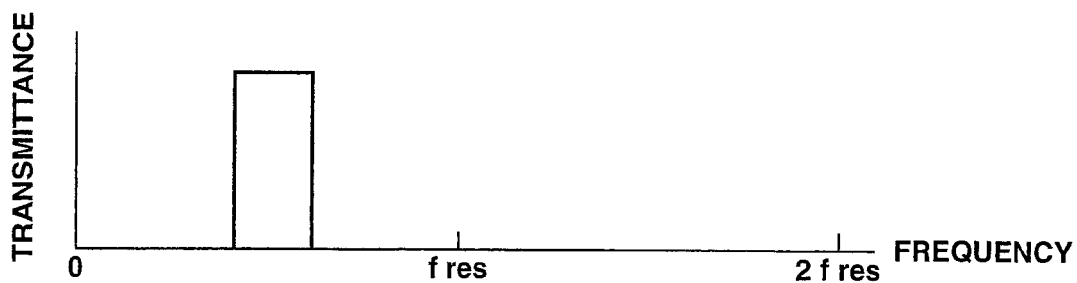
FIG. 10 is a view that shows an example of a passing frequency band in the filter processing section shown in FIG. 2.
Figure 11:
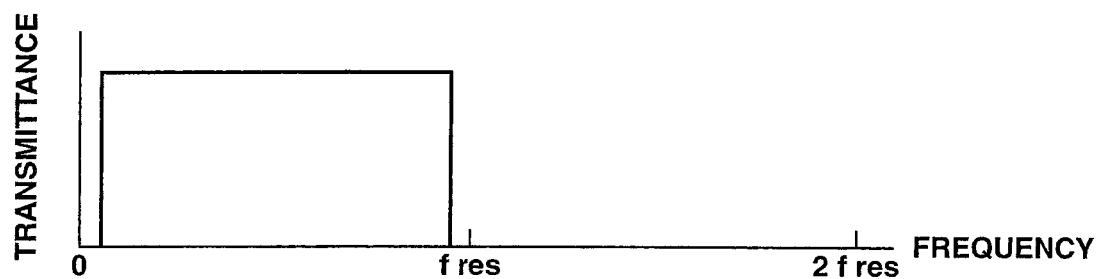
FIG. 11 is a view that shows an example of a passing frequency band in the filter processing section shown in FIG. 2, that is different to the example shown in FIG. 10.
Figure 12:
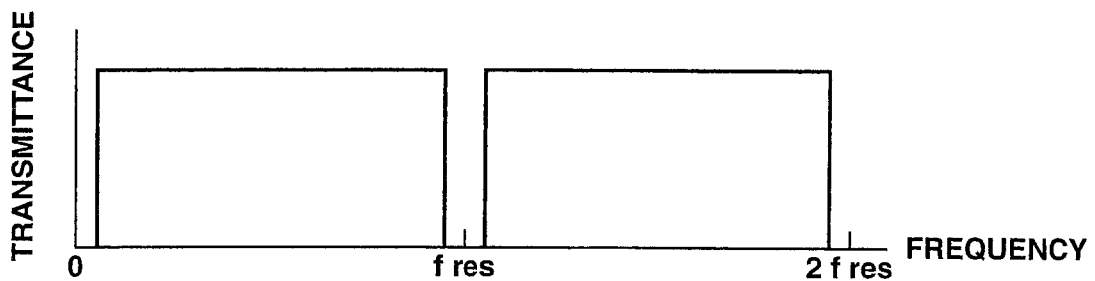
FIG. 12 is a view that shows an example of a passing frequency band in the filter processing section shown in FIG. 2, that is different to the examples shown in FIG. 10 and FIG. 11.

Based on control of the CPU 34, the filter processing section 33 switches the switches 33b1, 33b2, ..., 33bn, respectively, so that a passing frequency band in the bandpass filters 33a1, 33a2, ..., 33an becomes, for example, any one of the frequency bands shown in FIG. 10, FIG. 11, and FIG. 12.

FIG. 10 is a view that illustrates a case in which a passing frequency band at the bandpass filters 33a1, 33a2, ..., 33an is set so as to form a frequency band at one part on a low frequency side. More specifically, FIG. 10 illustrates a case in which a passing frequency band at the bandpass filters 33a1, 33a2, ..., 33an is set so as to form a frequency band that includes a subharmonic (divisor) of ½ of the resonance frequency fres.

FIG. 11 is a view that illustrates a case in which a passing frequency band at the bandpass filters 33a1, 33a2, ..., 33an is set from a frequency that is approximately 5% of the resonance frequency fres to a frequency that is 5% lower than the resonance frequency fres (i.e. a frequency that is 95% of the resonance frequency fres).

FIG. 12 is a view that illustrates a case in which passing frequency bands at the bandpass filters 33a1, 33a2, ..., 33an are set to the frequency band shown in FIG. 11 and also to a frequency band from a frequency that is 5% higher than the resonance frequency fres to a frequency that is 5% lower than a frequency (2 fres) of the second harmonic of the resonance frequency fres.

More specifically, a passing frequency band at the bandpass filters 33a1, 33a2, ..., 33an is set so as to exclude the resonance frequency of the ultrasound transducer 21a and to include at least a subharmonic of the resonance frequency.

The filter processing section 33 detects frequency components that pass the switches 33b1, 33b2, ..., 33bn that are in an "on" state at the wave detectors 33c1, 33c2, ..., 33cn, respectively, and after performing integration processing at the integrator 33d, the filter processing section 33 outputs the result of the integration processing as a cavitation detection signal to the CPU 34.

According to the detection result for magnitudes of a current exemplified in FIG. 9, there is a trend that as a generation amount of cavitations increases, the aforementioned level of subharmonics becomes higher. Therefore, under a condition that a passing frequency band is the same at the bandpass filters 33a1, 33a2, ..., 33an, the result of integration processing at the integrator 33d is a value that increases relatively accompanying an increase in a cavitation generation amount, and that decreases relatively accompanying a decrease in a cavitation generation amount. More specifically, the CPU 34 of the present embodiment performs processing and operations as described hereafter by detecting such fluctuations in the aforementioned value as fluctuations in the level of a cavitation detection signal.

Upon detecting that the switch 38c has been switched on, the CPU 34 performs settings to make the temperature of the distal end portion of the probe 23 and/or in the vicinity of the distal end portion the aforementioned third temperature so that a generation state of cavitations becomes the aforementioned third level. The CPU 34 then performs control to cause the heating apparatus 4 to operate at a higher output than at normal operation and to also cause the temperature reducing apparatus 5 to operate normally so that the temperature of the distal end portion of the probe 23 and/or in the vicinity of the distal end portion reaches and is maintained at the aforementioned third temperature, and so that a level of a cavitation detection signal that is outputted from the filter processing section 33 reaches and is maintained at the aforementioned third level. According to this control, because a rise in temperature caused by the heating function (heating means) of the ultrasound treatment handpiece 2 exceeds a decrease in temperature caused by the temperature reducing function (temperature reducing means), the temperature of the distal end portion of the probe 23 and in the vicinity of the distal end portion rises, and generation of cavitations at the treatment target region 101 is promoted. As a result, a generation amount of cavitations at the treatment target region 101 increases relatively, and a treatment speed with respect to the treatment target region 101 can be made a high speed.

Further, immediately after setting the cavitation generation state to the aforementioned third level, the CPU 34 outputs to the interface section 35 a first display control signal so as to cause a portion corresponding to an area from "0" to "high speed" of the indicator 37a to be colored uniformly or substantially uniformly. Further, while performing control to cause the level of the cavitation detection signal that is outputted from the filter processing section 33 to reach and be maintained at the aforementioned third level, as necessary the CPU 34 outputs a second display control signal to cause an area of the indicator 37b from "0" to a part corresponding to the level of the cavitation detection signal to be colored uniformly or substantially uniformly to the interface section 35. The display state of the indicator 37a thus enters a state that is in accordance with the first display control signal, and by the display state of the indicator 37b changing in real time in accordance with the second display control signal, a surgeon or the like can easily check whether or not the current cavitation generation state is a state that is suitable for a high-speed treatment speed.

Upon detecting that the switch 38a has been switched on, the CPU 34 performs settings to make the temperature of the distal end portion of the probe 23 and/or in the vicinity of the distal end portion the aforementioned first temperature so that a generation state of cavitations becomes the aforementioned first level. The CPU 34 then performs control to cause the heating apparatus 4 to operate normally and to also cause the temperature reducing apparatus 5 to operate at a higher output than at normal operation so that the temperature of the distal end portion of the probe 23 and/or in the vicinity of the distal end portion reaches and is maintained at the aforementioned first temperature, and so that a level of a cavitation detection signal that is outputted from the filter processing section 33 reaches and is maintained at the aforementioned first level. According to this control, because a decrease in temperature caused by the temperature reducing function (temperature reducing means) of the ultrasound treatment handpiece 2 exceeds a rise in temperature caused by the heating function (heating means), the temperature of the distal end portion of the probe 23 and in the vicinity of the distal end portion decreases, and generation of cavitations at the treatment target region 101 is suppressed. As a result, a generation amount of cavitations at the treatment target region 101 decreases relatively, and a treatment speed with respect to the treatment target region 101 can be made a low speed.

Further, immediately after setting the generation state of cavitations to the aforementioned first level, the CPU 34 outputs to the interface section 35 a first display control signal so as to cause a portion corresponding to an area from "0" to "low speed" of the indicator 37a to be colored uniformly or substantially uniformly. Further, while performing control to cause the level of the cavitation detection signal that is outputted from the filter processing section 33 to reach and be maintained at the aforementioned first level, as necessary the CPU 34 outputs the second display control signal to cause an area of the indicator 37b from "0" to a part corresponding to the level of the cavitation detection signal to be colored uniformly or substantially uniformly to the interface section 35. The display state of the indicator 37a thus enters a state that is in accordance with the first display control signal, and by the display state of the indicator 37b changing in real time in accordance with the second display control signal, a surgeon or the like can easily check whether or not the current cavitation generation state is a state that is suitable for a low-speed treatment speed.

As described in the foregoing, according to the operation system 1 of the present embodiment, a generation state (generation amount) of cavitations in the treatment target region 101 can be made an appropriate state that is in accordance with a treatment speed with respect to the treatment target region 101. Therefore, according to the operation system 1 of the present embodiment it is possible to stabilize the treatment capability of an apparatus that performs treatment with respect to the treatment target region 101 while utilizing cavitations (that are generated accompanying ultrasound vibrations) such as, for example, the ultrasound treatment handpiece 2.

Further, according to the operation system 1 of the present embodiment, it is possible to change a generation state (generation amount) of cavitations at the treatment target region 101 while maintaining an output level of ultrasound vibrations (output level of an ultrasound drive signal that is outputted from the ultrasound oscillation section 31) at the distal end portion of the probe 23 at a fixed level, that is, without particularly changing an amplitude of ultrasound vibrations at the ultrasound transducer 21a. Consequently, according to the operation system 1 of the present embodiment, a load that accompanies control with respect to the ultrasound transducer 21a can be reduced, and as a result the useful life of the ultrasound treatment handpiece 2 can be extended.

Application of the present embodiment is not limited to the operation system 1 shown in FIG. 1. For example, the present embodiment can also be applied in a substantially similar manner to an operation system 100 shown in FIG. 13. In this connection, hereunder, where appropriate, a description regarding portions that have the same configuration as those of the operation system 1 is omitted from the description of the operation system 100.

Figure 13:
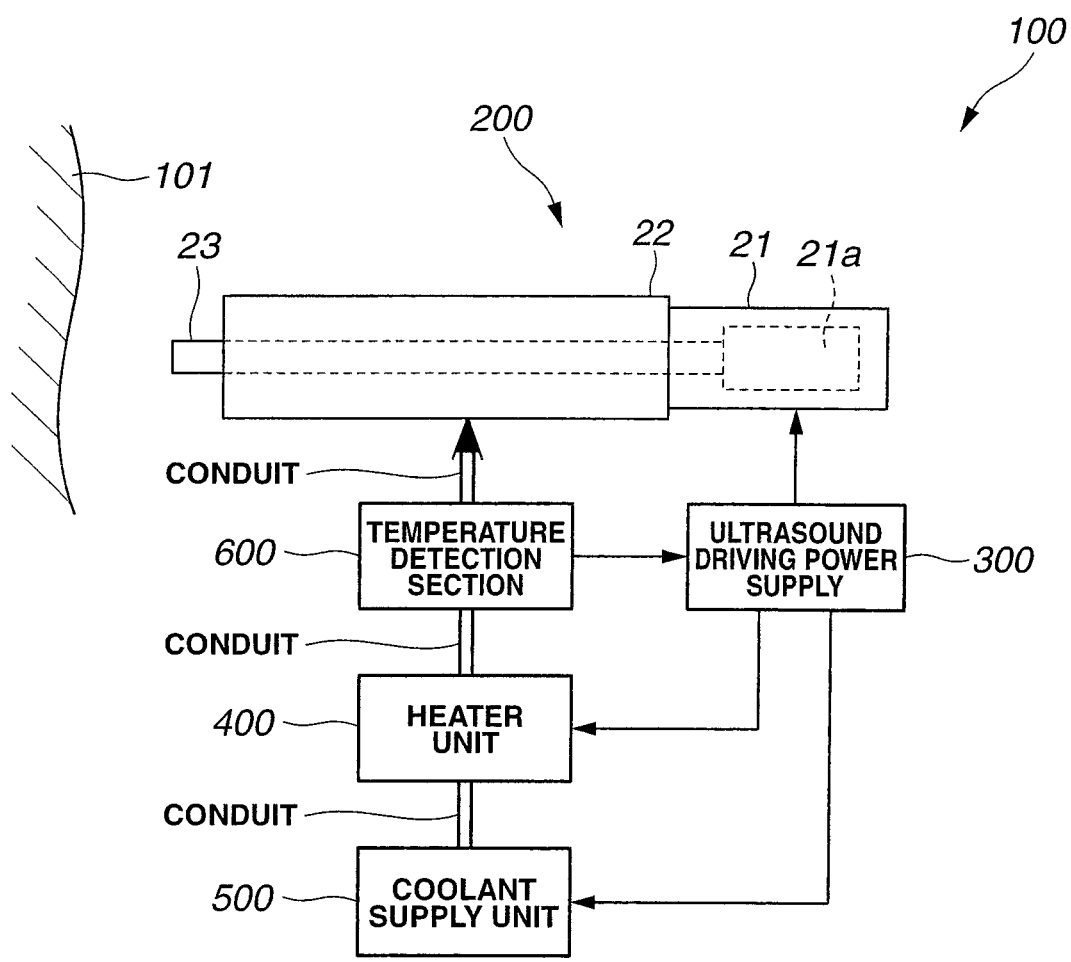
FIG. 13 is a view that shows an example of the configuration of an operation system according to the embodiment of the present invention that is different to the example shown in FIG. 1.

The operation system 100 shown in FIG. 13 is a configuration example in a case in which the functions (means) including a heating function (heating means), a temperature reducing function (temperature reducing means), and a temperature information output function (temperature information output means) are implemented outside an ultrasound treatment handpiece. More specifically, as shown in FIG. 13, the operation system 100 has an ultrasound treatment handpiece 200 that performs treatment by causing ultrasound vibrations to act on living tissue of the treatment target region 101, an ultrasound driving power supply 300 that supplies an ultrasound drive signal for driving the ultrasound treatment handpiece 200, a heater unit 400, a coolant supply unit 500, and a temperature detection section 600.

Instead of being equipped with the respective functions (means) of a heating function (heating means), a temperature reducing function (temperature reducing means), and a temperature information output function (temperature information output means), the ultrasound treatment handpiece 200 is equipped with an internal conduit (unshown) for allowing coolant that has passed through the temperature detection section 600 to circulate to the distal end portion of the probe 23 and/or a vicinity of the distal end portion.

The ultrasound driving power supply 300 has the same configuration as that of the ultrasound driving power supply 3. However, it is assumed that the following setting data is written in a memory 34a of the ultrasound driving power supply 300.

Setting data that sets a cavitation generation state to a first level when the switch 38a in the treatment speed switching section 38 is switched on is stored in the memory 34a of the ultrasound driving power supply 300. Further, setting data that sets a cavitation generation state to a second level when the switch 38b in the treatment speed switching section 38 is switched on is stored in the memory 34a of the ultrasound driving power supply 300. Furthermore, setting data that sets a cavitation generation state to a third level when the switch 38c in the treatment speed switching section 38 is switched on is stored in the memory 34a of the ultrasound driving power supply 300. In this connection, it is assumed that a relationship is established between each of these kinds of setting data such that the first level<second level<third level so that the amount of cavitations generated increases as the treatment speed becomes higher.

With respect to setting data that sets a cavitation generation state to the first level, as a setting that makes a temperature of the distal end portion of the probe 23 of the ultrasound treatment handpiece 200 and/or in a vicinity of the distal end portion a first temperature, for example, a setting is made that causes the heater unit 400 to operate normally and causes the coolant supply unit 500 to operate at a higher output than at normal operation. Further, with respect to setting data that sets a cavitation generation state to the second level, as a setting that makes a temperature of the distal end portion of the probe 23 of the ultrasound treatment handpiece 200 and/or in a vicinity of the distal end portion a second temperature, for example, a setting is made that causes both the heater unit 400 and the coolant supply unit 500 to operate normally. Furthermore, with respect to setting data that sets a cavitation generation state to the third level, as a setting that makes a temperature of the distal end portion of the probe 23 of the ultrasound treatment handpiece 200 and/or in a vicinity of the distal end portion a third temperature, for example, a setting is made that causes the heater unit 400 to operate at a higher output than at normal operation and causes the coolant supply unit 500 to operate normally. In this connection, it is assumed that a relationship is established for these settings such that the first temperature<second temperature<third temperature.

The CPU 34 of the ultrasound driving power supply 300 previously reads in (for example, immediately after the power of the ultrasound driving power supply 300 is turned on) each of the aforementioned kinds of setting data, and performs operational control with respect to the heater unit 400 and the coolant supply unit 500 based on a temperature signal that is outputted from the temperature detection section 600, a cavitation detection signal that is outputted from the filter processing section 33, and a switched state of each switch of the treatment speed switching section 38 provided in the interface section 35 while referring to the respective kinds of setting data read from the memory 34a.

The coolant supply unit 500 is configured to be capable of supplying a coolant such as a cooling liquid and/or a cooling gas to a conduit in accordance with control of the ultrasound driving power supply 300. More specifically, the coolant supply unit 500 is configured as a liquid cooling type unit that feeds cooling water that is accumulated in a tank by means of a roller pump that operates in accordance with control of the ultrasound driving power supply 300. Alternatively, the coolant supply unit 500 is configured as a gas cooling type unit that feeds coolant gas that is accumulated in a gas cylinder by means of a gas supply unit that operates in accordance with control of the ultrasound driving power supply 300. Alternatively, the coolant supply unit 500 is configured as an apparatus that combines both of the aforementioned types of units.

The heater unit 400 has a configuration that is capable of heating a coolant supplied from the coolant supply unit 500 by generating heat based on control of the ultrasound driving power supply 300. More specifically, the heater unit 400 includes at least one heater disposed at one location in the conduit on a route from the coolant supply unit 500 to the temperature detection section 600, and a driving power source for driving each heater in accordance with control of the ultrasound driving power supply 300.

The temperature detection section 600 is provided in the conduit on a route from the heater unit 400 to the ultrasound treatment handpiece 200. The temperature detection section 600 detects a temperature of coolant that passes through the heater unit 400 and is supplied to the ultrasound treatment handpiece 200, and outputs a detection result as a temperature signal to the ultrasound driving power supply 300.

More specifically, according to the configuration of the operation system 100, after coolant that is supplied from the coolant supply unit 500 passes in sequence through the heater unit 400, the temperature detection section 600, and the conduit inside the ultrasound treatment handpiece 200, the coolant flows to the distal end portion of the probe 23 and/or a vicinity of the distal end portion.

In this connection, according to the operation system 100, control and the like that is the same as that described with respect to the operation system 1 can be performed by the CPU 34 reading each piece of setting data that is written in the memory 34a of the ultrasound driving power supply 300. Consequently, a detailed description of control and the like performed at the operation system 100 is omitted here.

Thus, when the present embodiment is applied to the operation system 100, substantially the same advantages can be obtained as in the case in which the present embodiment is applied to the operation system 1.

The present invention is not limited to the embodiment described above, and naturally various modifications and applications are possible within a range that does not depart from the spirit and scope of the invention.

What is claimed is:

1. An operation system, comprising:
   a treatment section that performs treatment of a treatment target region of a treatment subject by causing ultrasound vibrations generated by an ultrasound transducer to act on the treatment target region;
   a physico-chemical parameter adjustment section that changes a physico-chemical parameter that contributes to promotion and suppression of generation of a thermal energy in the treatment section;
   a detection section that detects a generation state of cavitations at the treatment region;
   a treatment speed switching section that is configured to switch a treatment speed with respect to the treatment target region; and
   a control section that causes a generation amount of cavitations at the treatment target region to be larger than the predetermined amount when the treatment speed set by the treatment speed switching section is faster than a predetermined speed, and causes a generation amount of cavitations at the treatment target region to be smaller than the predetermined amount when the treatment speed switching section is slower than the predetermined speed, by controlling the physico-chemical parameter adjustment section based on a detection result at the detection section.

2. The operation system according to claim 1, comprising:
   a drive section that drives the ultrasound transducer by means of a drive signal; and
   a probe that has a proximal end portion that is mechanically connected with the ultrasound transducer, and a distal end portion that can cause the treatment section to be brought adjacent to or in contact with the treatment target region, the probe being configured to transmit ultrasound vibrations generated at the ultrasound transducer from the proximal end portion to the distal end portion.

3. The operation system according to claim 1, wherein:
   the detection section detects a generation state of cavitations at the treatment target region by detecting a magnitude of a current or a voltage at respective frequencies excluding a resonance frequency of the ultrasound transducer and including at least a subharmonic of the resonance frequency, based on a drive signal output from a drive section that drives the ultrasound transducer.

4. The operation system according to claim 1, further comprising:
   an indicator that is configured to present a generation state of cavitations at the treatment target region as visual information;
   wherein, the control section changes the visual information that is presented by the indicator as necessary in accordance with the generation state of cavitations at the treatment region that is detected at the detection section.

5. The operation system according to claim 1, wherein:
   the physico-chemical parameter is a temperature in a vicinity of the treatment section and/or the treatment section; and
   the physico-chemical parameter adjustment section comprises a temperature adjustment section that changes a temperature in the vicinity of the treatment section and/or the treatment section.

* * * * *